United States Patent [19]

Drivon et al.

[11] Patent Number: 5,804,687
[45] Date of Patent: Sep. 8, 1998

[54] PROCESS FOR THE MANUFACTURE OF HALO ESTERS OF CARBOXYLIC OR DICARBOXYLIC ACIDS

[75] Inventors: Gilles Drivon, Saint-Martin en Haut; Jean-Philippe Gillet, Brignais; Sophie Suc, Chaponost, all of France

[73] Assignee: Elf Atochem S.A., Puteaux, France

[21] Appl. No.: 589,582

[22] Filed: Jan. 22, 1996

Related U.S. Application Data

[63] Continuation of Ser. No. 208,114, Mar. 9, 1994, abandoned.

[30] Foreign Application Priority Data

Mar. 9, 1993 [FR] France .................................. 93 02698
Jul. 30, 1993 [FR] France .................................. 93 09435

[51] Int. Cl.$^6$ .................................................. C07C 69/52
[52] U.S. Cl. ................................... 560/223; 560/236
[58] Field of Search ........................... 560/223, 236

[56] References Cited

U.S. PATENT DOCUMENTS

| | | | |
|---|---|---|---|
| 2,830,078 | 4/1958 | Fekete ..................................... | 260/486 |
| 4,260,812 | 4/1981 | Beck ....................................... | 560/223 |
| 4,421,675 | 12/1983 | Sawicki .................................. | 502/150 |
| 4,434,297 | 2/1984 | Astrologes ............................. | 560/236 |
| 5,202,462 | 4/1993 | Yazawa et al. ......................... | 560/236 |
| 5,319,132 | 6/1994 | Ozarwa et al. ......................... | 560/236 |

FOREIGN PATENT DOCUMENTS

| | | |
|---|---|---|
| 0 101 526 | 2/1984 | European Pat. Off. . |
| 2 583 414 | 12/1986 | France . |
| 61-69742 | 4/1986 | Japan . |
| 2 123 408 | 2/1984 | United Kingdom . |

OTHER PUBLICATIONS

Patent Abstracts of Japan, vol. 10, No. 235 (C–366) (2291), Aug. 14, 1986 (Abstract of JP–A–61 069 742).

Primary Examiner—José G. Dees
Assistant Examiner—Jean F. Vollano
Attorney, Agent, or Firm—Millen, White, Zelano, & Branigan, P.C.

[57] ABSTRACT

A compound (Ia) or (Ib) is prepared by reacting, in a polar aprotic solvent, a compound (III) with a salt of a carboxylic or dicarboxylic acid (IIa) or (IIb). The reaction may be carried out under pressure, but also at normal atmospheric pressure or in the region of normal atmospheric pressure (especially between 0.10 bar and 2 bars). The product (Ia) or (Ib) formed is, in this latter case, recovered continuously as it is formed.

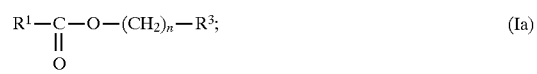

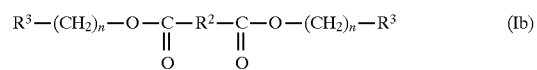

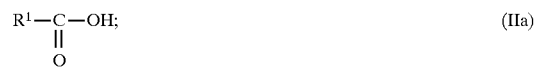

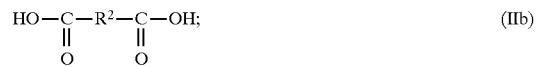

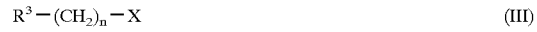

$R^1$, $R^2$=optionally substituted saturated or unsaturated acyclic or cyclic hydrocarbon radicals; $R^3$=$C_1$–$C_{10}$ perhaloalkyl; $0<n\leq4$; X=halogen.

The applications of the fluoroalkyl (meth)acrylates obtained are especially: anti-dust or anti-soiling paints for various supports such as exterior coatings and metal furniture; optical fibers; contact lenses; lithography; electrophotography; heat-resistant materials; dental resins.

16 Claims, No Drawings

PROCESS FOR THE MANUFACTURE OF HALO ESTERS OF CARBOXYLIC OR DICARBOXYLIC ACIDS

This application is a continuation of application Ser. No. 08/208,114, filed Mar. 9, 1994 abandoned.

The present invention relates to a new process for the manufacture of halo esters of carboxylic or dicarboxylic acids, represented by the general formula (Ia) or (Ib):

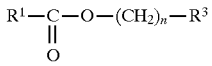 (Ia)

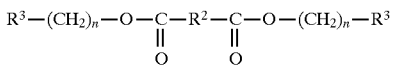 (Ib)

where:

$R^1$ represents an optionally substituted saturated or unsaturated acyclic or cyclic hydrocarbon radical;

$R^2$ represents an optionally substituted saturated or unsaturated acyclic or cyclic hydrocarbon radical;

$R^3$ represents a $C_1$–$C_{10}$ perhaloalkyl radical;

$0 < n \leq 4$.

Among these esters, there may more particularly be mentioned the compounds of formula (A):

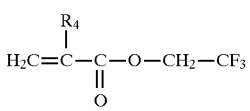 (A)

with $R_4$=methyl radical or hydrogen atom, which find applications in the following areas: anti-dust or anti-soiling paints for various supports such as exterior coatings and metal furniture; optical fibres; contact lenses; lithography; electrophotography; heat-resistant materials; dental resins.

From French Patent FR-B-2,583,414, a process is known for the preparation of these fluoroalkyl (meth)acrylates of formula (A), according to which process a (meth)acrylic anhydride of formula (a):

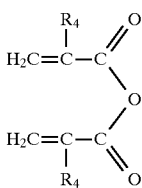 (a)

where $R_4$ is as defined above, is reacted with 2,2,2-trifluoroethanol, in the presence of a polymerization inhibitor and an acid catalyst, the molar ratio of the anhydride relative to the alcohol being between 0.5 and 5, and the resulting compound (A) is then separated out.

The compounds of formula (A), prepared in this way, are expensive products due to the high cost of 2,2,2-trifluoroethanol and the separation problems. A new, more economical synthesis route has thus been sought, from products available in industrial quantities.

Success has now been achieved in perfecting a new route of access to the compounds of formula (A) and, more generally, to the compounds of formula (Ia) and (Ib), by reaction, in a polar aprotic solvent, of a salt of a carboxylic (IIa) or dicarboxylic (IIb) acid:

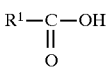 (IIa)

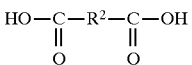 (IIb)

where $R^1$ and $R^2$ are as defined above, with a compound of formula (III):

 (III)

in which:

$R^3$ and n are as defined above; and

X represents a halogen.

It was not obvious that such a reaction could take place, on the one hand, because of the low reactivity of the compound (III) and, on the other hand, because of the risks of polymerization in the case of the unsaturated acids.

The subject of the present invention is thus a process for the manufacture of a compound represented by the formula (Ia) or (Ib) as defined above, characterized in that a compound of formula (III) as defined above is reacted, in a polar aprotic solvent, with a salt of a carboxylic or dicarboxylic acid of formula (IIa) or (IIb) as defined above.

This reaction may be carried out under pressure. In this case, the reaction may be carried out under a pressure approximately between 2 and 100 bars, advantageously approximately between 5 and 100 bars. The use of an inert gas (air or $N_2$) may be envisaged for bringing an additional pressure to the autogenous pressure of the system. After the reaction, the compound of formula (Ia) or (Ib) thus obtained is then separated from the reaction medium.

It has, however, been surprisingly discovered that this reaction could advantageously be carried out at normal atmospheric pressure or in the region of normal atmospheric pressure, for example under a pressure approximately between 0.10 bar and 2 bars, either by continuous introduction into the reactor of the compound (III) into a suspension, introduced into the reactor beforehand, of the salt of the acid (IIa) or (IIb) in the abovementioned solvent, or by continuous introduction into the reactor of the compound (III) and of the suspension of salt in the solvent, the product formed (Ia) or (Ib) being, in the two embodiments, recovered continuously as it is formed.

The advantages of an operation carried out at atmospheric pressure reside in the fact that it is not necessary to use pressure-resistant apparatus and that the compound (Ia) or (Ib) is recovered by continuous distillation as it is formed. This limits the undesired hydrolysis and dimerization side reactions, proportionally simplifying the final purification. Furthermore, this process provides total safety in so far as it is performed at normal atmospheric pressure or in the region of normal pressure and in so far as the risks of polymerization in the reactor are greatly reduced.

Among the salts of acids of formula (IIa) or (IIb), there may be mentioned, among others, those of acids in which:

$R^1$ represents a $C_1$–$C_6$ linear or branched alkyl radical; a $C_2$–$C_6$ alkenyl radical; an aryl radical such as a phenyl radical; and $R^2$ represents a radical —$(CH_2)_m$—, m being 1 to 6; a divalent $C_2$–$C_6$ alkenylene radical; or a divalent arylene radical such as a phenylene radical.

As salts of acids (IIa) or (IIb), an alkali metal salt such as, for example, that of Na, K, Rb or Cs, or an alkaline-earth metal salt such as that of Mg or Ca is used.

As compounds of formula (III), there may be mentioned those for which:

$R^3$ represents a $C_1$–$C_{10}$ perfluoroalkyl radical; and

X represents fluorine, chlorine, bromine or iodine.

Among the compounds of formula (III) there may especially be mentioned:

2-chloro-1,1,1-trifluoroethane;
1,2-dichloro-1,1-difluoroethane;
2-bromo-1,1,1-trifluoroethane;
1,2-dibromo-1,1-difluoroethane;
2-perfluorohexyl-1-iodoethane.

The polar aprotic solvent is chosen, for example, from the group consisting of sulpholane (tetramethylene sulphone), N,N-dimethylformamide, dimethyl sulphoxide, N,N-dimethylacetamide, N-methylpyrrolidone, 1,3-dimethyl-2-imidazolidinone, 1,3-dimethyl-3,4,5,6-tetrahydro-2-pyrimidinone and their mixtures. Sulpholane or 1,3-dimethyl-2-imidazolidinone is preferably used.

For improving the reaction kinetics it is advantageous to carry out this reaction in the presence of a phase transfer agent (crown ethers, polyethoxylated compounds such as oxyethylenated nonylphenol (marketed under the name ANTAROX CO 990) or tris[2-(2-methoxy-ethoxy)ethyl] amine, and so on), in an amount of 0.1 to 5 molar % relative to the salt of the acid of formula (IIa) or (IIb) employed.

Moreover, a molar ratio of the compound of formula (III) to the salt of the acid of formula (IIa) approximately between 0.2 and 10, preferably approximately between 1 and 7, and a molar ratio of the compound of formula (III) to the salt of the acid of formula (IIb) between 0.4 and 20, preferably between 2 and 12, are advantageously used. In addition, the concentration of the salt of the acid of formula (IIa) or (IIb) relative to the solvent is advantageously between 5 and 50% by weight, preferably between 10 and 40% by weight.

The reaction temperature is generally approximately between 50° and 280° C., preferably approximately between 120° and 240° C.

In addition, the reaction is carried out in the presence or absence of a stabilizing agent, for example N,N'-diphenyl-p-phenylenediamine.

In order to better illustrate the subject of the present invention, several implementation examples thereof will be described below, as a guide and with no limitation being implied. The percentages indicated in these examples are by weight, except where otherwise mentioned. The abbreviations used are the following:

TRIFEA: 2,2,2-trifluoroethyl acrylate
TRIFEMA: 2,2,2-trifluoroethyl methacrylate
TRIFEAC: 2,2,2-trifluoroethyl acetate
KA: potassium acrylate
KMA: potassium methacrylate
Forane 133a: 2-chloro-1,1,1-trifluoroethane
DPPD: N,N'-diphenyl-p-phenylenediamine (stabilizing agent)

EXAMPLE 1

Preparation of TRIFEMA by reaction of KMA with Forane 133a at atmospheric pressure 321 g of sulpholane, 0.08 g of DPPD and 40 g of KMA are introduced into a glass reactor of 500 cm³ capacity, fitted with a stirring device (turbine), a heating device and a system allowing regulation of the temperature. Heating is carried out at 210° C. with stirring and the Forane, 133a is then introduced continuously in gaseous form by means of an entry pipe at the foot of the reactor, at atmospheric pressure for 5 hours 30 minutes, at an average flow rate of approximately 39 g per hour. The TRIFEMA formed is recovered as it is formed by condensation at 15° C. of the gaseous "discharge".

82.6 g of a condensate consisting of 50.8 g of TRIFEMA, essentially mixed with Forane 133a, are recovered. The conversion of the KMA is 99.9% and the selectivity relative to the KMA converted is 94%.

All these results are determined by analysis of the reaction medium and of the condensates, by gas phase chromatography and by potentiometry.

EXAMPLES 2 to 4

Example 1 is repeated, under various conditions, as reported in Table 1 which follows. The results regarding the conversion and the selectivity are also indicated in Table 1.

TABLE 1

| Example | Sulpholane employed (g) | KMA employed (g) | Flow rate of the Forane 133a (g/hour) | Temperature (°C.) | Duration of the reaction | Quantity of stabilizing agent (g) | TRIFEMA (g) | Conversion of the KMA | Selectivity relative to the KMA |
|---|---|---|---|---|---|---|---|---|---|
| 2 | 266 | 40 | 38 | 220 | 4 h 15 min | 0.08 | 52.4 | 99.9 | 96.9 |
| 3 | 323.5 | 50 | 49.4 | 250 | 2 h 30 min | 0.10 | 58 | 99.1 | 87.3 |
| 4* | 323 | 50 | 53.4 | 210 | 4 h 15 min | 0.10 | 65.1 | 98.1 | 98 |

*The medium contains 2.5 mol % of 18-crown-6 crown eithwe relative to the KMA

EXAMPLE 5

Preparation of TRIFEAC from potassium acetate and Forane 133a at atmospheric pressure The procedure is performed as in Example 1, using 290 g of sulpholane and 39.3 g (0.401 mol) of potassium acetate in place of the KMA, and 39.6 g/h of Forane 133a are introduced at the temperature of 210° C. for 6 h 20 min.

52.4 g, equivalent to 0.37 mol, of $CH_3$—COO—$CH_2$—$CF_3$ are recovered, which corresponds to a conversion of 99.5% of the potassium acetate and a TRIFEAC selectivity of 92.5%.

EXAMPLE 6

Preparation of TRIFEAC from sodium acetate and Forane 133a at atmospheric pressure The procedure is performed as in Example 5, using 290 g of sulpholane and 16.4 g (0.2 mol) of sodium acetate, and the Forane 133a is introduced at 210° C. for 4 hours at a flow rate of 40 g/h.

5.25 g, equivalent to 0.037 mol, of $CH_3$—COO—$CH_2$—$CF_3$ are recovered, with a conversion of the sodium acetate of 21.5% and a TRIFEAC selectivity of 86%.

EXAMPLE 7

Preparation of trifluoroethyl benzoate from potassium benzoate and Forane 133a at atmospheric pressure The procedure is performed with the same apparatus as for the above examples. 290 g of sulpholane and 40 g (0.25 mol) of potassium benzoate are charged. Forane 133a is introduced for 5 hours at 240° C., at a flow rate of 40 g/h. 47.5 g (0.233 mol) of trifluoroethyl benzoate are recovered, with a conversion of the potassium benzoate of 99.7% and a selectivity of 93.5%.

EXAMPLES 8 to 14

Preparation of TRIFEMA by reaction of KMA with Forane 133a under pressure

EXAMPLE 8

39.5 g of KMA, 0.08 g of DPPD and 164.2 g of sulpholane are introduced into a 500 ml autoclave. 76.2 g of Forane 133a are subsequently introduced. Nitrogen is then introduced so that the pressure in the reactor reaches 5 bars. The reaction medium is heated at 210° C. for 1 hour. During this time, the pressure passes through a maximum of 23 bars to stabilize at 18 bars. After returning the autoclave to room temperature and then to atmospheric pressure, the reaction medium is analysed by gas phase chromatography and by potentiometry.

0.89 g of unreacted KMA is found, equivalent to a conversion of 97.7% of the KMA, and 45 g of TRIFEMA, equivalent to a selectivity relative to the KMA converted of 86%.

EXAMPLE 9

Example 8 is repeated, using 99.5 g of Forane 133a and 34.9 g of KMA.

0.97 g of unreacted KMA is found, equivalent to a conversion of 97.2% of the KMA, and 42.36 g of TRIFEMA, equivalent to a selectivity relative to the KMA converted of 92%.

EXAMPLE 10

Example 8 is repeated using the same ingredients as those of Example 1, but without the stabilizing agent (DPPD).

The reactants are used in the following amount:

44.67 g of Forane 133a 53.2 g of KMA.

8.85 g of unreacted KMA are found, equivalent to a conversion of 83.3% of the KMA, and 42.16 g of TRIFEMA, equivalent to a selectivity relative to the KMA converted of 70.3%.

EXAMPLE 11

Example 8 is repeated, but with introduction of nitrogen such that the initial pressure reaches 10 bars.

The reactants are used in the following quantity:

75.4 g of Forane 133a 38.9 g of KMA.

0.14 g of unreacted KMA is found, equivalent to a conversion of 99.7% of the KMA and 46.9 g of TRIFEMA, equivalent to a selectivity relative to the KMA converted of 89.1%.

EXAMPLE 12

Example 8 is repeated, but replacing the nitrogen with air. The following reactants were used:

76.5 g of Forane 133a 39.9 g of KMA.

9.9 g of KMA are found, equivalent to a conversion of 75.2% of the KMA, and 33.1 g of TRIFEMA, equivalent to a selectivity relative to the KMA converted of 81.4%.

EXAMPLE 13

Example 8 is repeated using the following operating conditions:

temperature 200° C.

0.008 g of DPPD duration of the reaction in order to have a stabilization of the pressure: 2 hours There are used:

29.3 g of Forane 133a 27 g of KMA.

After reaction, it is found that the conversion of the KMA is 74.3% for a TRIFEMA selectivity of 84.6%.

EXAMPLE 14

Example 13 is repeated using the following conditions:

initial nitrogen pressure: 10 bars temperature: 190° C.

duration of the reaction in order to have a stabilization of the pressure: 2 hours 29.6 g of Forane 133a 27.3 g of KMA.

After reaction, it is found that the conversion of the KMA is 56.4% for a TRIFEMA selectivity of 74.2%.

EXAMPLE 15

Preparation of TRIFEA by reaction of KA with Forane 133a under pressure 35 g of KA and 0.1 g of DPPD and 167 g of sulpholane are introduced into the same apparatus as for Example 1. 77.14 g of Forane 133a are subsequently introduced. Nitrogen is subsequently introduced such that the pressure in the reactor reaches 5 bars. The temperature of the reaction medium is brought to and maintained at 210° C. for 2 h 30 min.

After analysis, 7.45 g of KA are collected, equivalent to a conversion of 78.8% of the KA, and 23.9 g of TRIFEA, equivalent to a selectivity of 62% relative to the KA converted.

EXAMPLE 16

Example 15 is repeated, but without the DPPD and by using the following quantities of reactants:

47.85 g of KA 45.4 g of Forane 133a.

At the end of the reaction, 14.5 g of KA are collected, equivalent to a conversion of 70% of the KA, and 21.2 g of TRIFEA, equivalent to a selectivity of 45.5% relative to the KA.

We claim:

1. A process for the manufacture of a compound of the formula (Ia):

wherein:

$R^1$ represents an optionally substituted ethylenically unsaturated acyclic or cyclic hydrocarbon radical;

$R^3$ represents a $C_1$–$C_{10}$ perhaloalkyl radical;

n is 1, 2, 3 or 4 said process comprising reacting, in a polar aprotic solvent, a salt of a carboxylic acid of formula (IIa):

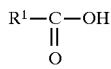  (IIa)

where the radical $R^1$ is as defined above, with a compound of formula (III):

  (III)

in which:

$R^3$ and n are as defined above; and

X represents a halogen, said reacting being conducted at 200°–250° C. and at a pressure of 0.1–2 bars, and continuously removing the resultant compound (Ia) from the reactor.

2. A process according to claim 1, characterized in that the reaction is carried out at normal atmospheric pressure.

3. A process according to claim 1, characterized in that the compound of formula (III) is introduced continuously into a reactor containing a previously provided suspension of the salt of the acid of formula (IIa) in the polar aprotic solvent, the product formed (Ia) being recovered continuously as it is formed.

4. A process according to claim 1, wherein the compound (III) and a suspension of the salt of the acid of formula (IIa) in the polar aprotic solvent are introduced at the same time and continuously into the reactor, the product formed, (Ia), being recovered continuously as it is formed.

5. A process according to claim 1, wherein the pressure of 0.1–2 bars in the reaction is provided by a combination of the autogenous pressure of the system and the use of an inert gas.

6. A process according to claim 1, wherein, after reaction, the compound of formula (Ia) obtained is separated from the reaction medium.

7. A process according to claim 1, characterized in that a salt of an acid (IIa) is used in which:

$R^1$ represents a $C_2$–$C_6$ alkenyl radical.

8. Process according to claim 1, characterized in that an alkali metal salt or alkaline-earth metal salt is used as salt.

9. A process according to claim 1, characterized in that a compound of formula (III) is used in which:

$R^3$ represents a $C_1$–$C_{10}$ perfluoroalkyl radical; and

X represents fluorine, chlorine, bromine or iodine.

10. Process according to claim 9, characterized in that 2-chloro-1,1,1-trifluoroethane, 1,2-dichloro-1,1-difluoroethane, 2-bromo-1,1,1-trifluoroethane, 1,2-dibromo-1,1-difluoroethane or 2-perfluorohexyl-1-iodo-ethane is used as compound of formula (III).

11. A process according to claim 1, characterized in that the polar aprotic solvent is chosen from sulpholane, N,N-dimethylformamide, dimethyl sulphoxide, N,N-dimethylacetamide, N-methylpyrrolidone, 1,3-dimethyl-2-imidazolidinone, 1,3-dimethyl-3,4,5,6-tetrahydro-2-pyrimidinone and their mixtures.

12. A process according to claim 1, characterized in that the reaction is carried out in the presence of at least one phase transfer agent, in an amount of 0.1 to 5 molar % relative to the salt of the acid of formula (IIa) employed.

13. A process according to claim 1, wherein the reaction is carried out with a molar ratio of the compound of formula (III) to the salt of the acid of formula (IIa) between 0.2 and 10.

14. A process according to claim 1, characterized by the fact that the procedure is performed at a concentration of the salt of the acid (IIa) between 5 and 50% by weight relative to the solvent.

15. A process according to claim 1, characterized in that the reaction is carried out in the presence of at least one stabilizing agent.

16. A process according to claim 15, wherein the stabilizing agent is N,N'-diphenyl-p-phenylenediamine.

* * * * *